United States Patent
Cook

(10) Patent No.: US 8,827,663 B2
(45) Date of Patent: Sep. 9, 2014

(54) ROTARY STABILITY OF A ROTARY PUMP

(71) Applicant: Thoratec Coporation, Pleasanton, CA (US)

(72) Inventor: Martin Christopher Cook, Coogee (AU)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/720,609

(22) Filed: Dec. 19, 2012

(65) Prior Publication Data

US 2013/0108489 A1    May 2, 2013

Related U.S. Application Data

(63) Continuation of application No. 12/577,936, filed on Oct. 13, 2009, now Pat. No. 8,353,686, which is a continuation of application No. 10/967,492, filed on Oct. 18, 2004, now abandoned.

(51) Int. Cl.
   *F04D 29/04*    (2006.01)
(52) U.S. Cl.
   USPC .............. 417/410.1; 417/420; 417/423.1; 415/110; 310/90.5; 310/268
(58) Field of Classification Search
   CPC . F04D 29/047; F04D 29/048; F04D 29/0413; F04D 13/066; H02K 7/09; H02K 7/14
   USPC ............. 417/410.1, 420, 423.1; 415/110; 310/90.5, 268
   See application file for complete search history.

(56) References Cited

U.S. PATENT DOCUMENTS

| | | |
|---|---|---|
| 4,957,504 A | 9/1990 | Chardack |
| 5,112,202 A | 5/1992 | Oshima et al. |
| 5,211,546 A | 5/1993 | Isaacson et al. |
| 5,220,259 A | 6/1993 | Werner et al. |
| 5,289,821 A | 3/1994 | Schwartz |
| 5,370,509 A | 12/1994 | Golding et al. |
| 5,695,471 A | 12/1997 | Wampler |
| 5,725,357 A | 3/1998 | Nakazeki et al. |

(Continued)

FOREIGN PATENT DOCUMENTS

| | | |
|---|---|---|
| CA | 2237203 | 9/2007 |
| EP | 1 354 606 | 10/2003 |

(Continued)

OTHER PUBLICATIONS

Ayre et al., "Identifying physiologically significant pumping states in implantable rotary blood pumps using invasive system observers", Proc. of 25th Annual Inter. Conf. of IEEE, pp. 439-442 (2003).

(Continued)

*Primary Examiner* — Charles Freay
*Assistant Examiner* — Patrick Hamo
(74) *Attorney, Agent, or Firm* — Squire Patton Boggs (US) LLP

(57) ABSTRACT

A rotary pump including an impeller rotatable within a housing. A load is imposed on the impeller as it rotates, in a direction that is substantially parallel to the axis of rotation and wherein the load stabilises the motion of the impeller. The load may be achieved by magnetically biasing the impeller.

8 Claims, 4 Drawing Sheets

(56) References Cited

U.S. PATENT DOCUMENTS

| | | |
|---|---|---|
| 5,840,070 A | 11/1998 | Wampler |
| 5,947,703 A | 9/1999 | Nojiri et al. |
| 6,015,434 A | 1/2000 | Yamane |
| 6,027,498 A | 2/2000 | Mutch et al. |
| 6,066,086 A | 5/2000 | Antaki et al. |
| 6,068,588 A | 5/2000 | Goldowsky |
| 6,071,093 A | 6/2000 | Hart |
| 6,074,180 A | 6/2000 | Khanwilkar et al. |
| 6,080,133 A | 6/2000 | Wampler |
| 6,100,618 A | 8/2000 | Schoeb et al. |
| 6,120,537 A | 9/2000 | Wampler |
| 6,158,984 A | 12/2000 | Cao et al. |
| 6,217,541 B1 | 4/2001 | Yu |
| 6,227,797 B1 | 5/2001 | Watterson et al. |
| 6,234,772 B1 | 5/2001 | Wampler et al. |
| 6,234,998 B1 | 5/2001 | Wampler |
| 6,264,635 B1 | 7/2001 | Wampler et al. |
| 6,277,078 B1 | 8/2001 | Porat et al. |
| 6,302,661 B1 | 10/2001 | Khanwilkar et al. |
| 6,368,083 B1 | 4/2002 | Wampler |
| 6,394,769 B1 | 5/2002 | Bearnson et al. |
| 6,395,026 B1 | 5/2002 | Aboul/Hosn et al. |
| 6,547,530 B2 | 4/2003 | Ozaki et al. |
| 6,575,717 B2 | 6/2003 | Ozaki et al. |
| 6,609,883 B2 * | 8/2003 | Woodard et al. ............... 415/107 |
| 6,623,420 B2 | 9/2003 | Reich et al. |
| 6,634,224 B1 | 10/2003 | Schob et al. |
| 6,640,617 B2 | 11/2003 | Schob et al. |
| 6,688,861 B2 | 2/2004 | Wampler |
| 6,709,382 B1 | 3/2004 | Horner |
| 6,711,943 B1 | 3/2004 | Schob et al. |
| 6,949,066 B2 | 9/2005 | Bearnson et al. |
| 6,991,595 B2 | 1/2006 | Burke et al. |
| 7,138,776 B1 | 11/2006 | Gauthier et al. |
| 7,141,943 B2 | 11/2006 | Song et al. |
| 7,494,459 B2 | 2/2009 | Anstadt et al. |
| 7,591,777 B2 | 9/2009 | LaRose |
| 7,645,225 B2 | 1/2010 | Medvedev et al. |
| 7,748,964 B2 | 7/2010 | Yaegashi et al. |
| 2001/0009645 A1 | 7/2001 | Noda |
| 2002/0183628 A1 | 12/2002 | Reich et al. |
| 2004/0084398 A1 | 5/2004 | Breitschwerdt et al. |
| 2004/0084399 A1 | 5/2004 | Cook et al. |
| 2004/0152944 A1 | 8/2004 | Medvedev et al. |
| 2004/0234397 A1 | 11/2004 | Wampler et al. |
| 2005/0208095 A1 | 9/2005 | Hunter et al. |
| 2006/0149331 A1 | 7/2006 | Mann et al. |
| 2007/0231135 A1 | 10/2007 | Wampler et al. |
| 2008/0080983 A1 | 4/2008 | Wampler et al. |
| 2008/0085184 A1 | 4/2008 | Wampler et al. |
| 2008/0089779 A1 | 4/2008 | Wampler et al. |
| 2008/0089797 A1 | 4/2008 | Wampler et al. |

FOREIGN PATENT DOCUMENTS

| | | |
|---|---|---|
| JP | 2002-224066 | 8/2002 |
| JP | 2004-278375 | 10/2004 |
| WO | WO 97/29795 | 8/1997 |
| WO | WO 01/05023 | 1/2001 |
| WO | WO 01/12070 | 2/2001 |
| WO | WO 01/72352 | 10/2001 |
| WO | WO 03/015609 | 2/2003 |
| WO | WO 2004/028593 | 4/2004 |
| WO | WO 2010/101107 | 9/2010 |

OTHER PUBLICATIONS

Barletta et al. "Design of a bearingless blood pump", Proceedings from Third Int. Symposium on Magnetic Suspension Technology, Ed. By Nelson J. Groom and Colin P. Britcher Jul. 1996, pp. I-XIII and 265-274.

Yamazaki et al., Development of a Miniature Intraventricular Axial Flow Blood Pump, ASAIO J. 1993, pp. M224-M230.

* cited by examiner

ROTARY STABILITY OF A ROTARY PUMP

CROSS-REFERENCE TO RELATED APPLICATIONS

This application is a continuation of U.S. patent application Ser. No. 10/967,492, filed Oct. 18, 2004, and is incorporated by reference herein in its entirety.

TECHNICAL FIELD

The present nvention relates to improvements in the impeller or rotor stability of a rotary pump.

BACKGROUND OF THE INVENTION

Rotary pumps have used journal bearings to stabilise a spinning rotor or impeller. It has been noted that commonly the impeller rotates about a central axis within the pump housing and may whirl to the side of the housing when the impeller is rotated at high speeds with insufficient load and results in instability in relation to the rotation of the impeller.

The impeller of the rotary blood pump disclosed within U.S. Pat. No. 6.227,797—Watterson et al. is hydrodynamically suspended and may under certain conditions the impeller or rotor may experience a touchdown event. A touchdown event is a situation where the impeller or rotor touches or contacts the inner walls of the pump housing. Touchdown of the impeller or rotor often leads to damaging the impeller, housing and/or the pumping fluid. If a touchdown event occurs in a rotary blood pump implanted in a patient such an event may result in impaired pump performance that may result in complications for the patient. Touchdown may be avoided by increasing the stability of the impeller or rotor or increasing the stiffness and/or dampening of the impeller or rotor.

U.S. Pat. No. 5,324,177—Golding et at describes a means for increasing impeller or rotor stability in a rotary pump. The impeller and/or rotor are biased by a load provided by additional load acting only in radial orientation in respect of the axis of rotation of the pump. This has the effect of offsetting the rotor and thus stabilising the rotor in only the radial direction. The arrangement disclosed in U.S. Pat. No. 5,324,177, may also tend to destabilise the impeller in relation to the axial positioning of the impeller. Additionally, the radial biasing of the impeller is only useful in situations where the motor stators of the pump are positioned radially in respect of the axis of rotation of the impeller. This may lead to a considerably increase in size of the overall pump.

The present invention aims to at least address or ameliorate one or more of the above disadvantages associated with the abovementioned prior art.

SUMMARY OF THE INVENTION

In accordance with a first aspect the present invention consists in a rotary pump including an impeller rotatable within a housing; wherein a load is imposed on said impeller as it rotates, in a direction that is substantially parallel to the axis of rotation and wherein said load stabilises the motion of the impeller.

Preferably said load is achieved by magnetically biasing said impeller.

Preferably said pump includes a set of stators positioned below the impeller and said set of stators generates said load.

Preferably the magnetically biasing of said impeller is achieved by at least one yoke. Preferably an angle formed between the upper and/or lower axial surfaces of the impeller are not parallel with the respective corresponding surface of the inner wall of the housing.

Preferably said impeller is not circular and the inner walls of the housing are generally circular.

Preferably said load prevents or limits the impeller from contacting the housing, when in use.

Preferably said impeller is generally square shaped.

Preferably said impeller includes a hydrodynamic bearing.

Preferably said hydrodynamic bearing is formed by a taper on the surface of the impeller of between 101 m and 50 gm.

Preferably a gap of less than 250 gm is formed between the impeller and the housing. when in use.

Preferably said pump is for pumping blood.

Preferably said pump is implantable within the body of a patient.

In accordance with a second aspect the present invention consists in a rotary pump including an impeller rotatable within a housing; wherein impeller is hydrodynamically suspended and wherein an angle formed between the upper and/or lower axial surfaces of the impeller are not parallel with the respective corresponding surface of the inner wall of the housing.

BRIEF DESCRIPTION OF DRAWINGS

Embodiments of the present invention will now be described with reference to the accompanying drawing wherein.

DETAILED DESCRIPTION OF THE PREFERRED EMBODIMENT

Figure 1:
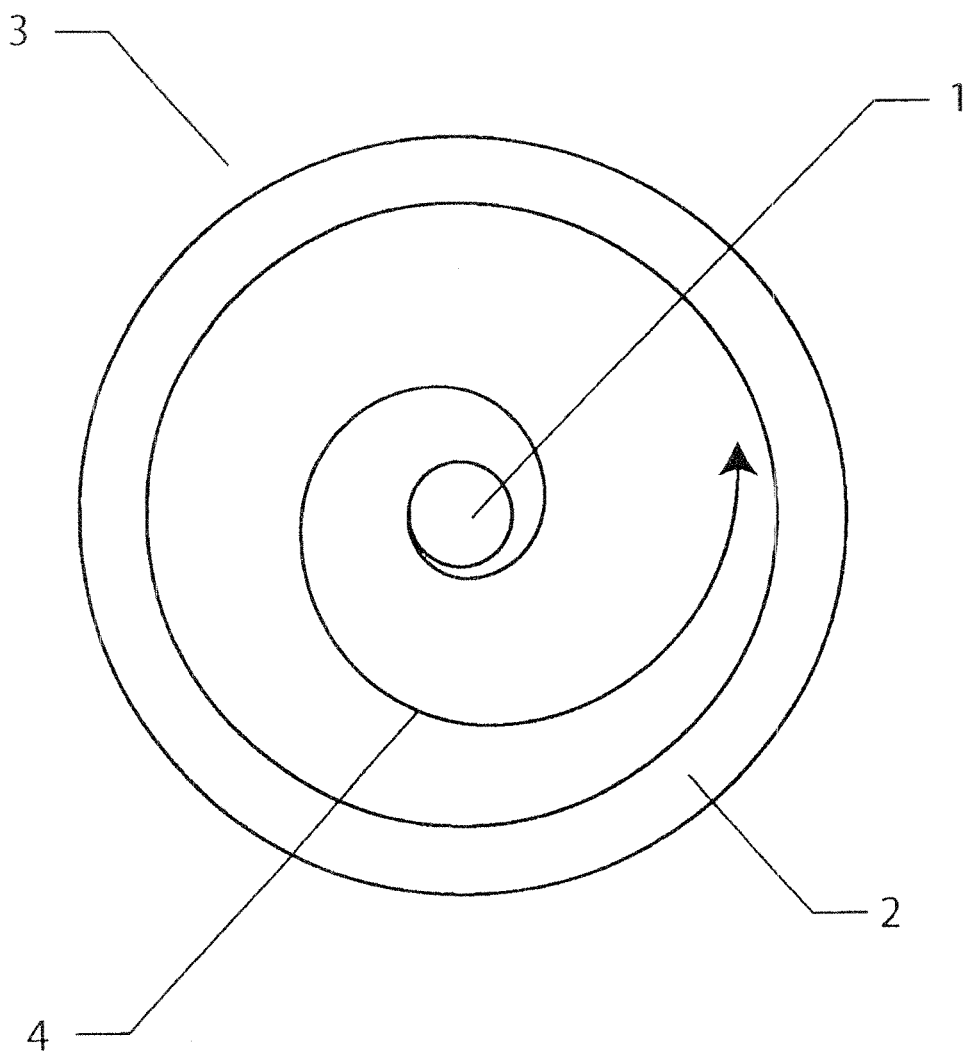
FIG. 1 shows a cross-sectional top view of an example of the prior art in this field.

FIG. 1 schematically depicts a prior art rotary pump 3 having a generally circular impeller 1 positioned within a pump housing 2 with a generally circular inner wall. The impeller 1 is preferably suspended by a fluid or hydrodynamic bearing generated by the interaction of the outer surface of impeller 1 and the inner surface of pump housing 2.

The impeller 1 rotates about a central axis of the rotary pump 3. In FIG. 1, the impeller 1 is shown to be under an insufficient biasing load. This insufficient load biasing the impeller 1 allows it to move away from the central axis of rotation in a helical pattern 4. This results in the impeller 1 experiencing a relative instability which in the worst case may lead to impeller instability. The impeller 1 may in this case roll around the inner surface of the housing 2 and follow the helical path 4. which may lead to the eventual collision with the inner wall of the housing 2. This on may result in damage to the outer surfaces of the impeller 1 against the inner walls of the housing 2 and/or damaging the pumping fluid.

Figure 2:
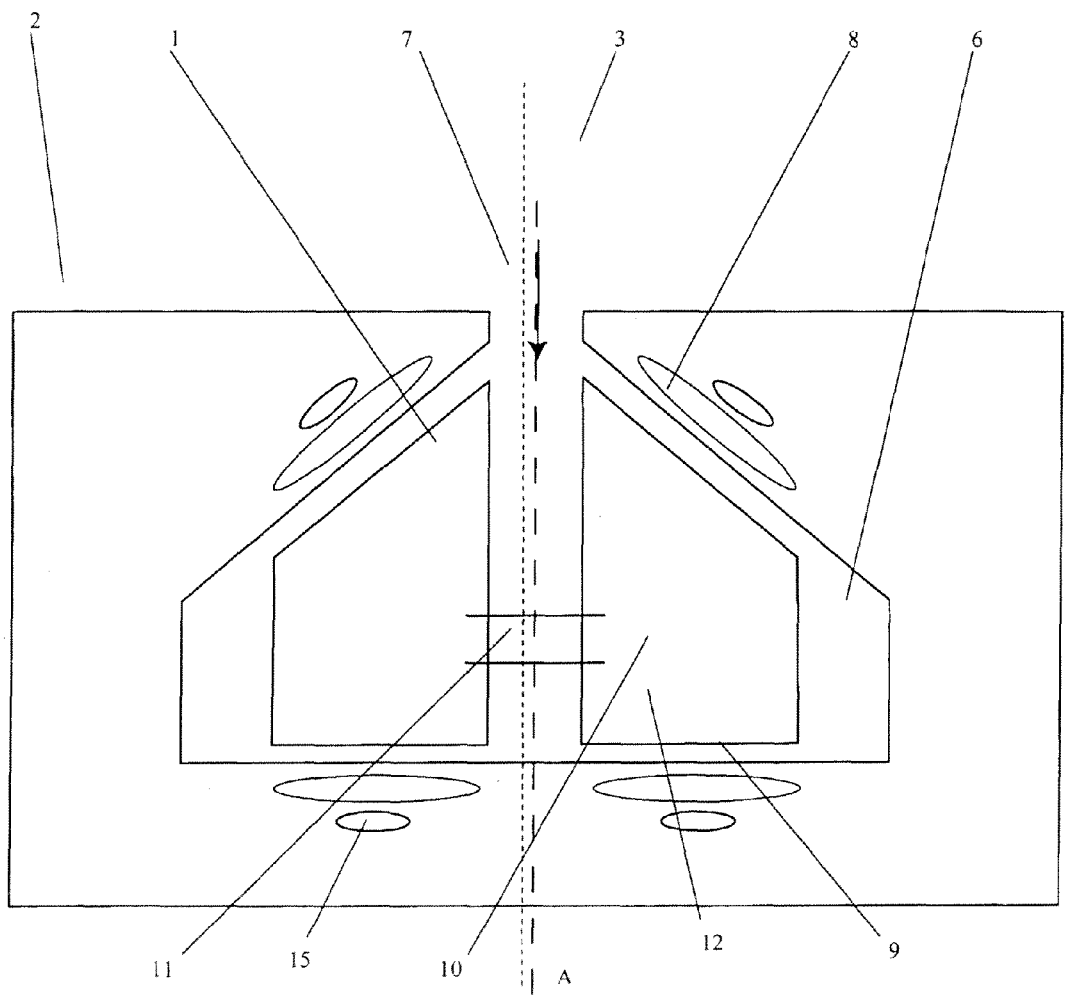
FIG. 2 shows a cross-sectional side view of a first embodiment of the present invention.

A first embodiment of the present invention is shown in FIG. 2. In this embodiment, there is provided a rotary pump 3 including an impeller 1 which is hydrodynamically suspended within housing 2 using a fluid bearing. When in use, the impeller 1 rotates about the axis of rotation and pumps fluid from the inlet 7 to the outlet 6 by a continuous centrifugal motion, The pumping fluid is preferably blood and the rotary pump 3 is suitable for implantation within the body a patient.

The fluid bearing is achieved by the interaction of the outer surface of the impeller 1 interacting with the inner surface of the housing 2 of the rotary pump 3. The rotary pump 3 is preferably adapted to be implantable within the body of a patient to assist the pumping fluid, such as blood. The rotary pump 3 includes: stators 9, an inlet 7, and an outlet 6. The stators 9 are preferably mounted axially, in relation to the axis of rotation of the rotary pump 3, on or in the housing 2 and impart an electrodynamic driving force on magnets encapsulated within each of the blades 10 which form the impeller 1. The impeller 1 comprises four blades 10 that are connected by struts 11 in a generally square configuration and the blades 10 also include hydrodynamic bearing surfaces which form fluid bearings when they interact with the inner surface of the housing.

When in use, a load may be created electromagnetically by the stators 9 to act on the impeller 1 in a direction that is substantially parallel to the axis of rotation A. This load acts on the impeller 1 in an axial direction and biases the impeller 1 either generally towards the inlet 7 or towards the lower inner surface of the housing 2. The axial biased load acting on the impeller 1 may additionally stabilise the rotating impeller 1 and may improve the stability of impeller 1.

The electromagnetic biasing may be achieved by either: increasing the EMF output of the stators on either the upper or lower side of the impeller 1; or by introducing a yoke which contacts the stators and increases the EMF output on either the upper or lower side of the impeller 1.

Alternately, the load may be created by inducing an axial magnetic load. This magnetic load may be formed or created by including a ring of iron or Permalloy™ material above and/or below the stators 9 in the housing. The ring may form a yoke 15 covering the stators 9. Preferably, the ring on either side of the impeller 1 must be of varying amounts of iron or be of varying distances from the impeller 1. The effect of which would be to vary the load experienced by the impeller 1 as the magnets encapsulated with the impeller 1 may be drawn to a yoke 15.

Preferably, the gap 8 is formed between the outer axial surface of the impeller 1 and the corresponding inner wall of the housing 2. The gap 8 is preferable optimised when the gap 8 is less than 250 gm, as this may increase stiffness and dampening of the hearing and lead to increases in rotor stability.

Also preferably, the blades 10 of the impeller 1 include a tapered surface. The tapered surface is preferably optimised at a height of between 101 m and 50 gm. This also may allow the impeller or rotor o be additionally stabilised.

Figure 3:
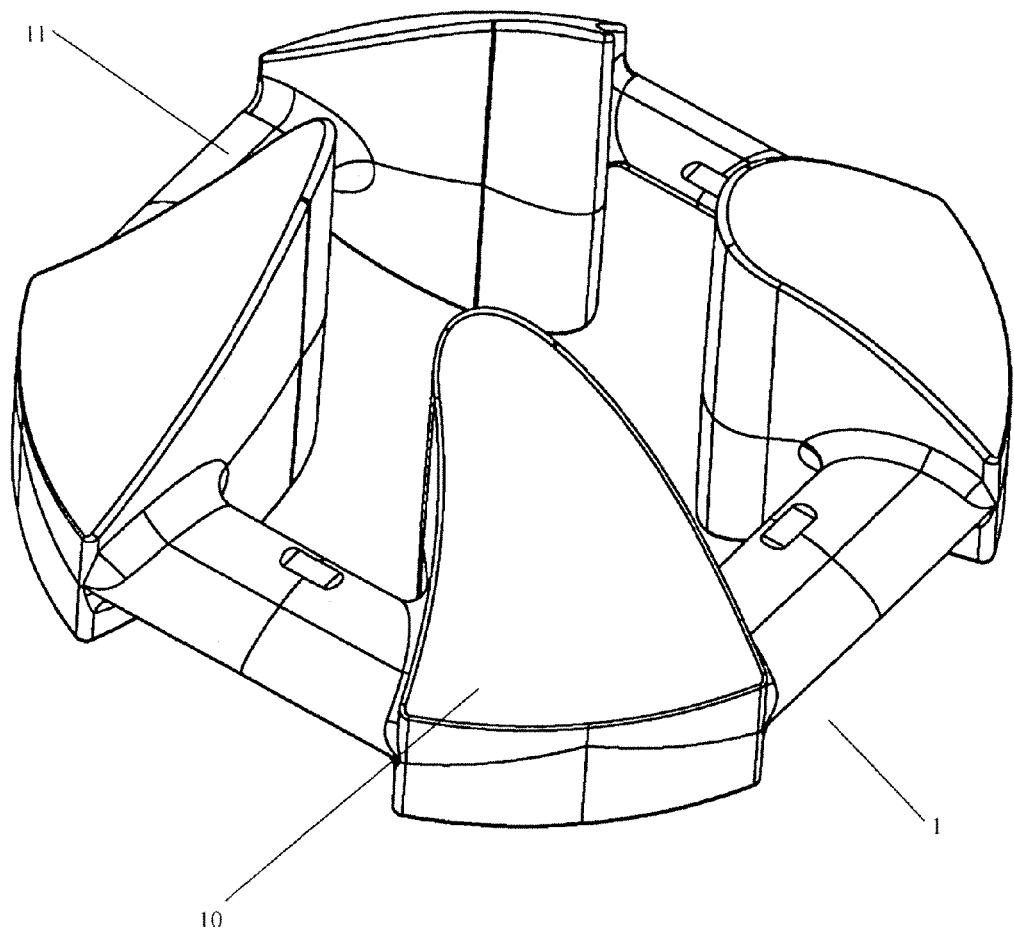
FIG. 3 shows a perspective view of a portion part of the embodiment shown in FIG. 2.

FIG. 3 shows a preferred impeller 1 which may be used with the first embodiment of the present invention. This impeller 1 includes four blades 10 joined by four struts 11. The blades 10 may include hydrodynamic surfaces to allow the impeller 1 to be hydrodynamically suspended, when in use. The blades 10 preferably have a generally 'shark fin' shaped configuration so as to minimise damage to the pumping fluid. The impeller 1 has a generally square configuration. wherein the struts 11 are joined between the outer adjacent edges of the blades 10. The struts 11 may also include hydrodynamic surfaces. The preferred impeller 1 is shaftless to also minimise damage to the pumping fluid.

Figure 4:
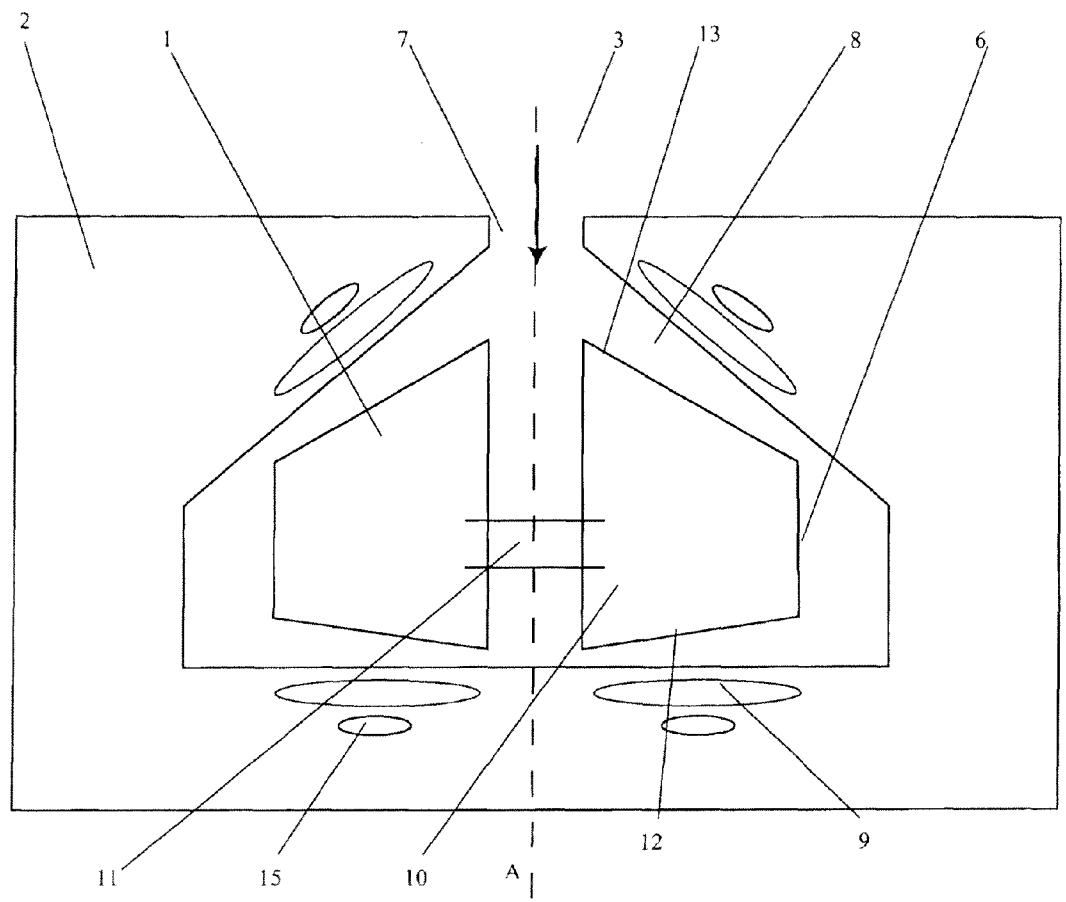
FIG. 4 shows a cross-sectional side view of a second embodiment of the present invention.

The impeller 10 shown in FIG. 3, may also experience an additional load, when in use. This load may be generated by the generally square configuration of the impeller 10 interacting with a generally circular interior surface of the pump housing 2. The non-uniform shape of the impeller 10, as depicted FIG. 3, may allow the forces acting on the impeller to be decentralised and this may increase the load acting on the impeller 10. The load thereby limits the instability experienced by the impeller 10. A further embodiment of the present invention is shown in FIG. 4. This embodiment shows an alternate impeller 1, wherein the upper 13 and lower 12 axial outer surfaces of the impreller 1 have been positioned to be not parallel with the respective corresponding surface of the inner of the housing 2. The effect of this feature is to increase the stiffness and dampening of the bearing, when in use. This in turn leads to an increase in relation to the stability of the rotor or impeller 1 and may prevent or limit touchdown.

The embodiment shown in FIG. 4 could be achieved by using the embodiment shown in FIG. 2 and rotating the blades 10 inwards towards the centre of the impeller 1. The inward angle depends on the position of the center of gravity relative to the center of pressure on the bearing surface of the A person skilled in the art will recognise that the term impeller within this specification has substantially the same meaning as rotor. All of the preferred embodiments may be used as implantable medical devices or as cardiac assist devices.

The above descriptions describe only some of the embodiments of the present invention. Further modifications may be obvious to those skilled in art and may be made without departing from the scope and spirit of the present nvention.

The invention claimed is:

1. A rotary pump, comprising:
a housing having an upper and lower innermost surface;
a shaftless impeller rotatable within the housing, the impeller including a plurality of blades having upper and lower outermost surfaces, wherein an axial hydrodynamic bearing is formed between the outermost surfaces of the blades and innermost surfaces of the housing when a fluid is conveyed through the housing, and
wherein the outermost surfaces of the blades are non-parallel with the respective innermost surfaces of the housing, thereby forming a tapered gap between the blades and the housing; and
a loading device configured to impose a magnetic biasing load on the impeller as the impeller rotates, in a direction that is substantially parallel to the axial direction;
wherein the combination of the magnetic biasing load and the hydrodynamic bearing stabilizes the motion of the impeller.

2. The rotary pump of claim 1, further including a set of electromagnets configured to create the magnetic biasing load, the electromagnets being located below or above the impeller and configured to bias the impeller generally towards an inlet of the rotary pump or a lower surface of the housing.

3. The rotary pump of claim 2, wherein the biasing load is created by either increasing the EMF output of the stators or placing a yoke in contact with the stators.

4. The rotary pump of claim 1, wherein the biasing load is created by an induced magnetic load, wherein the induced magnetic load is formed by an iron or PERMALLOY material located above and/or below stators in the housing.

5. The rotary pump of claim 1, wherein a gap separating hydrodynamic bearing surfaces formed by the outermost surface of the impeller and opposing surface of the housing is less than 250 micro-meters.

6. The rotary pump in claim 1, wherein the outermost surfaces of the blades are tapered.

7. The rotary pump in claim 6, wherein the outermost surfaces are tapered and defined by a curvilinear boundary such that the outermost surfaces are generally shark-fin like in appearance, wherein at least the generally shark-fin like surfaces opposing the walls of the housing defines with the walls of the housing the tapered gap.

8. The rotary pump in claim 1, further including an upper tapered gap present at upper outermost surfaces of the blades, and a lower tapered gap present at lower outermost surfaces of the blades, wherein the upper tapered gap is greatest at a radial inward location and the lower tapered gap is greatest at a radial outward location.

* * * * *